United States Patent
Li (10) Patent No.: US 9,884,835 B2
(45) Date of Patent: Feb. 6, 2018

(54) METHOD FOR PREPARING ISOBENZOFURAN-1(3H)-ONE COMPOUND

(71) Applicant: Everfront Biotech Inc., New Taipei (TW)

(72) Inventor: Wen-Sen Li, New Taipei (TW)

(73) Assignee: EVERFRONT BIOTECH INC., New Taipei (TW)

( * ) Notice: Subject to any disclaimer, the term of this patent is extended or adjusted under 35 U.S.C. 154(b) by 0 days.

(21) Appl. No.: 15/518,467

(22) PCT Filed: Oct. 14, 2015

(86) PCT No.: PCT/CN2015/091929
§ 371 (c)(1),
(2) Date: Apr. 11, 2017

(87) PCT Pub. No.: WO2016/058532
PCT Pub. Date: Apr. 21, 2016

(65) Prior Publication Data
US 2017/0260155 A1    Sep. 14, 2017

Related U.S. Application Data

(60) Provisional application No. 62/064,529, filed on Oct. 16, 2014.

(51) Int. Cl.
C07D 307/88 (2006.01)
C07C 51/087 (2006.01)
C07C 51/363 (2006.01)
C07C 51/48 (2006.01)
C07C 51/42 (2006.01)

(52) U.S. Cl.
CPC .......... C07D 307/88 (2013.01); C07C 51/087 (2013.01); C07C 51/363 (2013.01); C07C 51/42 (2013.01); C07C 51/48 (2013.01)

(58) Field of Classification Search
CPC .................................................. C07D 307/88
USPC ........................................................ 549/307
See application file for complete search history.

(56) References Cited

FOREIGN PATENT DOCUMENTS

CN        1086814 A      5/1994
WO     2012080243 A2    6/2012

OTHER PUBLICATIONS

Hemmi; Biochemistry 1985, 24, 1841-1848.*
Britton; Org. Process Res. Dev., 2012, 16, 1607-1617.*
(Continued)

*Primary Examiner* — Daniel R Carcanague
(74) *Attorney, Agent, or Firm* — McClure, Qualey & Rodack, LLP

(57) ABSTRACT

A method for preparing an isobenzofuran-1(3H)-one based compound of the following formula I is provided. R1, R2 and p are defined in the specification.

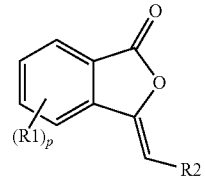

formula I

17 Claims, 4 Drawing Sheets

(56) References Cited

OTHER PUBLICATIONS

Yang; Bioorganic & Medicinal Chemistry Letters 2007, 17, 5210-5213.*
He; Tetrahedron Letters 2014, 55, 1956-1958.*
Kanazawa; Tetrahedron Letters 2007, 48, 933-935.*
Ciattini, Pier Giuseppe et al. "A New Synthesis of 3-Ylidenephthalides via Palladium-Catalyzed Cyclocarbonylation of 2-Triflyloxyacetophenones", Tetrahedron Letters, vol. 34, No. 23, Jun. 4, 1993 (Jun. 4, 1993) ISSN: 0040-4039, pp. 3763-3766, see the specific reaction equation and table 3 of p. 3764.
Krafft, Grant A. et al. "Synthesis of Halo Enol Lactones. Mechanism-Based Inactivators of Serine proteases" Journal of the American Chemical Society, vol. 103, No. 18, Sep. 30, 1981 (Sep. 30, 1981) ISSN: 0002-7863, pp. 5459-5466, see specific schemas 5, see the third paragraph to the sixth paragraph from the bottom in right column of p. 5465.
Benneche, Tore et al., "Synthesis of 5-(Bromomethylene) furan-2 (5H)-ones and 3-(Bromomethylene) isobenzofuran-1 (3H)-ones as Inhibitors of Microbial Quorum Sensing" New Journal of Chemistry, vol. 32, No. 9, May 12, 2008 (May 12, 2008) ISSN:1144-0546, pp. 1567-1572, see specific schemas 2 and 4.
International Search Report and Written Opinion for PCT/CN2015/091929, dated Jan. 11, 2016.

\* cited by examiner

METHOD FOR PREPARING ISOBENZOFURAN-1(3H)-ONE COMPOUND

BACKGROUND OF THE INVENTION

Field of the Invention

The present invention relates to a method for preparing an isobenzofuran-1(3H)-one based compound, especially a method for preparing (Z)-3-butylidene isobenzofuran-1(3H)-one, i.e., (Z)-n-butylidenephthalide.

Descriptions of the Related Art 3-butylidene isobenzofuran-1(3H)-one (molecular formula: $C_{12}H_{12}O_2$; molecular weight: 188.22) is a monoterpene compound useful for treating various tumors, such as glioblastoma multiforme and mammary cancer (see Tsai et al., Clin. Cancer Res. 2005, 11(9): 3475-3484 and Tsai et al., J Neurochem. 2006, 99(4): 1251-62). In the past, 3-butylidene isobenzofuran-1(3H)-one has been isolated from the extracts of Angelica sinensis. However, the isolated product is a mixture comprising both (Z)-3-butylidene isobenzofuran-1(3H)-one and (E)-3-butylidene isobenzofuran-1(3H)-one component, and it is difficult to further separate (Z)-3-butylidene isobenzofuran-1(3H)-one from (E)-3-butylidene isobenzofuran-1(3H)-one component. Therefore, all commercially available 3-butylidene isobenzofuran-1(3H)-one are a mixture of (Z)-3-butylidene isobenzofuran-1(3H)-one and (E)-3-butylidene isobenzofuran-1(3H)-one. If such mixture is used in the pharmaceutical industry, it would be difficult to control the impurities.

In view of the above, the present invention provides a synthetic method for preparing an isobenzofuran-1(3H)-one based compound, especially for preparing (Z)-3-butylidene isobenzofuran-1(3H)-one.

SUMMARY OF THE INVENTION

An objective of the present invention is to provide a method for preparing a compound of the following formula I:

formula I

The method comprises the following steps:
(I) reacting a halogenated carboxylic acid anhydride with a compound of the following formula (1) at a first temperature ranging from about 50° C. to about 140° C. to obtain a compound of the following formula (2); and formula (1)

formula (2)

(II) reacting the compound of formula (2) with a compound of (R2)MgX at a second temperature ranging from about −10° C. to about 10° C. to obtain the compound of formula I, wherein, each R1 is independently C1-C10 alkyl, C3-C10 cycloalkyl or C6-C20 aryl;

R2 is C1-C20 alkyl;

X is Cl⁻, Br⁻ or I⁻; and p is an integer ranging from 0 to 3.

In some embodiments of the present invention, R2 is propyl and p is 0.

In some embodiments of the present invention, the first temperature ranges from about 100° C. to about 130° C.

In some embodiments of the present invention, the second temperature ranges from about −5° C. to about 5° C.

In some embodiments of the present invention, the halogenated carboxylic acid anhydride is selected from the group consisting of monofluoroacetic anhydride, difluoroacetic anhydride, trifluoroacetic anhydride, pentafluoropropionic anhydride, heptafluorobutyric anhydride, perfluoropentanoic anhydride, perfluorohexanoic anhydride, chlorodifluoroacetic anhydride, monochloroacetic anhydride, dichloroacetic anhydride, trichloroacetic anhydride, pentachloropropionic anhydride, heptachlorobutyric anhydride, perchloropentanoic anhydride, perchlorohexanoic anhydride, and combinations thereof. The halogenated carboxylic acid anhydride is preferred to be trifluoroacetic anhydride.

In some embodiments of the present invention, the reaction of step (I) is carried out in toluene, and the reaction of step (II) is carried out in an inert solvent selected from the group consisting of diethyl ether, tetrahydrofuran (THF), 2-methyl tetrahydrofuran, and combinations thereof.

In some embodiments of the present invention, the method further comprises the following purification steps prior to step (II): extracting the reaction product of step (I) with ethyl acetate, collecting the organic phase, and filtering the organic phase and concentrating the obtained filtrate to obtain the compound of formula (2).

In some embodiments of the present invention, the method further comprises the following purification steps after step (II): mixing the reaction product of step (II) with ice water to provide a first mixture with a pH value of about 5 to 7; extracting the first mixture with ethyl acetate and collecting the organic phase; and filtering the organic phase and concentrating the obtained filtrate to obtain the compound of formula I.

In some embodiments of the present invention, the compound of formula (1) is provided with the following steps:

(I-1) reacting a compound of the following formula (3) with a malonic acid in the presence of a tertiary amine at a third temperature ranging from about 50° C. to about 90° C. to obtain a compound of the following formula (4); and formula (3)

formula (4)

(I-2) reacting the compound of formula (4) with a brominating agent in a carboxylic acid at a fourth temperature ranging from about 30° C. to about 50° C. to obtain the compound of formula (1).

The tertiary amine is preferably a trialkyl amine such as triethylamine or a trialkoxyamine. The brominating agent is preferably selected from the group consisting of bromine, pyridinium tribromide, N-bromosuccinimide and combinations thereof. Pyridinium tribromide is preferred. The carboxylic acid is selected from the group consisting of formic acid, acetic acid, propionic acid, butyric acid and combinations thereof. Acetic acid is preferred.

The method preferably further comprises the following purification steps prior to the step (I-2): extracting the reaction product of step (I-1) with ethyl acetate and collecting the organic phase; filtering the organic phase and concentrating the obtained filtrate; mixing the concentrated filtrate with ethyl acetate and heating the resultant mixture to a temperature between about 50° C. and about 60° C. to provide a second mixture; and cooling the second mixture to room temperature and mixing the same with n-hexane to precipitate the compound of formula (4). The pH value of the reaction product of step (I-1) is preferred to be adjusted to about 5 to 7 prior to the extraction with ethyl acetate.

The method preferably further comprises the following purification steps after step (I-2): extracting the reaction product of step (I-2) with ethyl acetate and collecting the organic phase; and filtering the organic phase and concentrating the obtained filtrate to obtain the compound of formula (1).

To render the above objects, technical features and advantages of the present invention more apparent, the present invention will be described in detail with reference to some embodiments hereinafter.

DESCRIPTION OF THE PREFERRED EMBODIMENT

Hereinafter, some embodiments of the present invention will be described in detail with reference to the appended drawings. However, without departing from the spirit of the present invention, the present invention may be embodied in various embodiments and should not be limited to the embodiments described in the specification and drawings. Unless it is additionally explained, the expressions "a," "the," or the like recited in the specification of the present invention (especially in the claims) should include both the singular and plural forms.

The present invention provides a method for preparing an isobenzofuran-1(3H)-one based compound, especially a method for preparing (Z)-3-butylidene isobenzofuran-1(3H)-one. Unlike the existing method which can only isolate a mixture of (Z)-3-butylidene isobenzofuran-1(3H)-one and (E)-3-butylidene isobenzofuran-1(3H)-one from the extracts of *Angelica sinensis*, the present invention could directly synthesize (Z)-3-butylidene isobenzofuran-1(3H)-one.

Specifically, the present invention provides a method for preparing a compound of formula I:

formula I

The method comprises the following steps:
(I) reacting a halogenated carboxylic acid anhydride with a compound of the following formula (1) at a first temperature to obtain a compound of the following formula (2); and formula (1)

formula (2)

(II) reacting the compound of formula (2) with a compound of (R2)MgX at a second temperature to obtain the compound of formula I,
wherein,
each R1 is independently selected from the following group: C1-C10 alkyl, such as methyl, ethyl, n-propyl, isopropyl, n-butyl, sec-butyl, tert-butyl, n-pentyl, neopentyl, tert-amyl, n-hexyl, n-octyl and tort-octyl; C3-C10 cycloalkyl, such as cyclopropyl, cyclobutyl, cyclopentyl and cyclohexyl; and C6-C20 aryl, such as phenyl, tolyl and xylyl;
R2 is C1-C20 alkyl, such as methyl, ethyl, n-propyl, isopropyl, n-butyl, sec-butyl, tert-butyl, n-pentyl, neopentyl, tert-amyl, n-hexyl, n-octyl, n-decyl, n-dodecyl, n-pentadecyl and n-eicosyl, and preferably methyl, ethyl, n-propyl, isopropyl, tert-butyl and tert-amyl;

X is Cl$^-$, Br$^-$ or I$^-$; and p is an integer ranging from 0 to 3.

In step (I), the halogenated carboxylic acid anhydride is reacted with the compound of formula (1) at a first temperature to obtain the compound of formula (2). The first temperature may be any temperature at which the halogenated carboxylic acid anhydride could react with the compound of formula (1). For example, in the case of preparing (Z)-3-butylidene isobenzofuran-1(3H)-one (an embodiment of the compound of formula I where R2 is propyl and p is 0), the first temperature may range from about 50° C. to about 140° C., preferably about 100° C. to about 130° C. and more preferably about 110° C. to about 130° C. It is found that a high reaction temperature such as a temperature over 100° C. could significantly reduce the formation of by-products other than the compound of formula (2) and therefore is advantageous to the yield of the compound of formula I.

The halogenated carboxylic acid anhydride may be any halogenated carboxylic acid anhydride that can react with the compound of formula (1). For example, the halogenated carboxylic acid anhydride may be selected from but are not limited to the group consisting of monofluoroacetic anhydride, difluoroacetic anhydride, trifluoroacetic anhydride, pentafluoropropionic anhydride, heptafluorobutyric anhydride, perfluoropentanoic anhydride, perfluorohexanoic anhydride, chlorodifluoroacetic anhydride, monochloroacetic anhydride, dichloroacetic anhydride, trichloroacetic anhydride, pentachloropropionic anhydride, heptachlorobutyric anhydride, perchloropentanoic anhydride, perchlorohexanoic anhydride, and combinations thereof. In the following example, the compound of formula (1) is 2-(2-bromoacetyl)benzoic acid and the halogenated carboxylic acid anhydride is trifluoroacetic anhydride.

In step (II), the compound of formula (2) is reacted with a compound with the general formula of (R2)MgX at a second temperature to obtain the compound of formula I. Without being limited by any theories, it is believed that (R2)MgX acts like an Grignard reagent to replace "Br" in the formula (2) with "R2" through couple action. Examples of (R2)MgX include but are not limited to CH$_3$MgF, C$_2$H$_5$MgF, C$_3$H$_7$MgF, C$_4$H$_9$MgF, CH$_3$MgCl, C$_2$H$_5$MgCl, C$_3$H$_7$MgCl, C$_4$H$_9$MgCl, CH$_3$MgBr, C$_2$H$_5$MgBr, C$_3$H$_7$MgBr, C$_4$H$_9$MgBr, CH$_3$MgI, C$_2$H$_5$MgI, C$_3$H$_7$MgI and C$_4$H$_9$MgI. The second temperature may be any temperature capable of conducting such a couple action. For example, in the case of preparing (Z)-3-butylidene isobenzofuran-1(3H)-one, the second temperature is preferably about −10° C. to about 10° C., and more preferably about −5° C. to about 5° C. The inert solvent used in the step (II) may be any solvent that is suitable for conducting such a couple action and can dissolve but not react with the compound of formula (2) and the compound of (R2)MgX. Without departing from the above selection conditions, examples of the inert solvent may include diethyl ether, tetrahydrofuran (THF), 2-methyl tetrahydrofuran and any combinations thereof. In the following example, the compound of (R2)MgX is C$_3$H$_7$MgCl, the second temperature is about 0° C., and the inert solvent is THF.

The method of the present invention may optionally comprise purification steps prior to or after step (II) to increase the purity of product. The purification steps can be performed prior to step (II) to purify the reaction product of step (I) and isolate the compound of formula (2), or can be performed after step (II) to purify the reaction product of step (II) and isolate the compound of formula I. For example, the following purification steps can be performed prior to step (II): extracting the reaction product of step (I) with ethyl acetate and collecting the organic phase; and filtering the organic phase and concentrating the obtained filtrate to obtain the compound of formula (2). After the reaction of step (II), the following purification steps can be performed: mixing the reaction product of step (II) with ice water to provide a first mixture with a pH value of 5 to 7, preferably 6; extracting the first mixture with ethyl acetate and collecting the organic phase; and filtering the organic phase and concentrating the obtained filtrate to obtain the compound of formula I. Without being restricted by any theories, it is believed that the aforementioned pH value is helpful in improving the yield. The purification steps will be exemplarily described in the following example in detail.

The compound of formula (1) used in step (I) is commercial available from relevant chemical suppliers. As an alternative, it can be provided by the following steps:

(I-1) reacting a compound of the following formula (3) with a malonic acid in the presence of a tertiary amine at a third temperature ranging from about 50° C. to about 90° C. to obtain a compound of the following formula (4); and formula (3)

formula (4)

(I-2) reacting the compound of formula (4) with a brominating agent in a carboxylic acid at a fourth temperature ranging from about 30° C. to about 50° C., and preferably about 35° C. to about 45° C., to obtain the compound of formula (1).

In step (I-1), the tertiary amine is not particularly limited. Examples of tertiary amine include but are not limited to trialkyl amines and trialkoxyamines. In the following example of the present invention, the tertiary amine is triethylamine. In the step (I-2), the brominating agent may be any agent that is capable of brominating the compound of formula (4) to obtain the compound of formula (1). Examples of the bromating agent include but are not limited to bromine, pyridinium tribromide, N-bromosuccinimide and any combinations thereof. Without being restricted by any theories, it is believed that the carboxylic acid could provide an acidic environment suitable for the bromating reaction. Examples of the carboxylic acid include but are not limited to formic acid, acetic acid, propionic acid, butyric acid and any combinations thereof. In the following example of the present invention, the third temperature is about 80° C., the fourth temperature is about 40° C., the bromating agent is pyridinium tribromide, and the carboxylic acid is acetic acid.

Similarly, purifications steps can be performed prior to or after step (I-2). The purification steps can be performed prior to step (I-2) to purify the reaction compound of step (I-1) and isolate the compound of formula (4), or can be performed after step (I-2) to purify the reaction compound of step (I-2) and isolate the compound of formula (1). For example, the following purification steps can be performed prior to step (I-2): extracting the reaction product of step (I-1) with ethyl acetate and collecting the organic phase; filtering the organic phase and concentrating the obtained filtrate; mixing the concentrated filtrate with ethyl acetate and heating the resultant mixture to a temperature between about 50° C. and about 60° C. to provide a second mixture; and cooling the second mixture to room temperature and mixing the same with n-hexane to precipitate the compound of formula (4). It is preferred to adjust the pH value of the reaction compound of formula (I-1) to about 5 to about 7 prior to the extraction with ethyl acetate. Without being restricted by any theories, it is believed that the aforementioned pH value is helpful in improving the yield. After the reaction of step (I-2), the following purification steps can be performed: extracting the reaction product of step (I-2) with ethyl acetate and collecting the organic phase; and filtering the organic phase and concentrating the obtained filtrate to obtain the compound of formula (1). The purification steps will be exemplarily described in the following example in detail.

Based on the above, an example of the present invention provides a method for preparing (Z)-3-(bromomethylene) isobenzofuran-1(3H)-one. The method comprises the following steps:

(I) reacting a halogenated carboxylic acid anhydride with 2-(2-bromoacetyl)benzoic acid at a first temperature to obtain (Z)-3-(bromomethylene)isobenzofuran-1(3H)-one; and (II) reacting the (Z)-3-(bromomethylene)isobenzofuran-1 (3H)-one with a compound having the general formula of $(C_3H_7)MgX$ at a second temperature to obtain (Z)-3-(bromomethylene)isobenzofuran-1(3H)-one, wherein, the first temperature, second temperature, and X are as previously defined, and purifications steps may be further carried out prior to or after step (II).

The present invention will be further illustrated by the example hereinafter. It will be understood that the above example is only for the purpose of illustration, rather than a limitation to the present disclosure. The scope of protection of the present invention is that as defined in the claims as appended.

Example: Preparation of (Z)-3-Butylideneisobenzofuran-1(3H)-One

Step (I-1): Preparation of 2-Acetylbenzoic Acid

Phthalic anhydride (CAS No.: 85-44-9; 100 g, 0.67 moles), a portion of malonic acid (CAS No.: 141-82-2; 0.3 eq, 21 g), and a portion of triethylamine (CAS No.: 121-44-8; 1.5 eq, 140 mL) were added into a reactor (a 1-liter three-neck bottle), and the resultant mixture in the reactor was heated to 65° C. The reaction was performed under 65° C. for 20 minutes to obtain a yellow transparent homogeneous solution.

The rest of the malonic acid (1 eq, 70 g) was divided into three portions and slowly added portionwise into the reactor within 30 minutes. Afterwards, the rest of the triethylamine (0.5 eq, 50 mL) was added to rinse any residual chemicals on the side wall of the reactor. The resultant mixture in the reactor was heated to 80° C. and the reaction was performed under 80° C. for 20 hours (the completion of reaction was determined by an NMR instrument). The reaction equation is as follows:

In the above reaction equation, compound 1 represents phthalic anhydride, compound 2 represents 2-acetylbenzoic acid, and $Et_3N$ represents triethylamine.

The reactor was cooled to room temperature after the completion of reaction. 4 N HCl solution (CAS No.: 7647-01-0) was added slowly into the reactor to adjust the pH value of the mixture therein to about 5 to about 6, and the pH-adjusted mixture was then stirred for 30 minutes. The resultant product was extracted with ethyl acetate (CAS No.: 141-78-6; 100 mL×4) and the organic phase was collected. The collected organic phase was washed with saturated brine (CAS No.: 7647-14-5) and saturated sodium bicarbonate (CAS No.: 144-55-8) aqueous solution to adjust the pH value to about 7, dried over anhydrous sodium sulfate (CAS No.: 7757-82-6), and then concentrated in vacuum to obtain the crude product.

Figure 1:
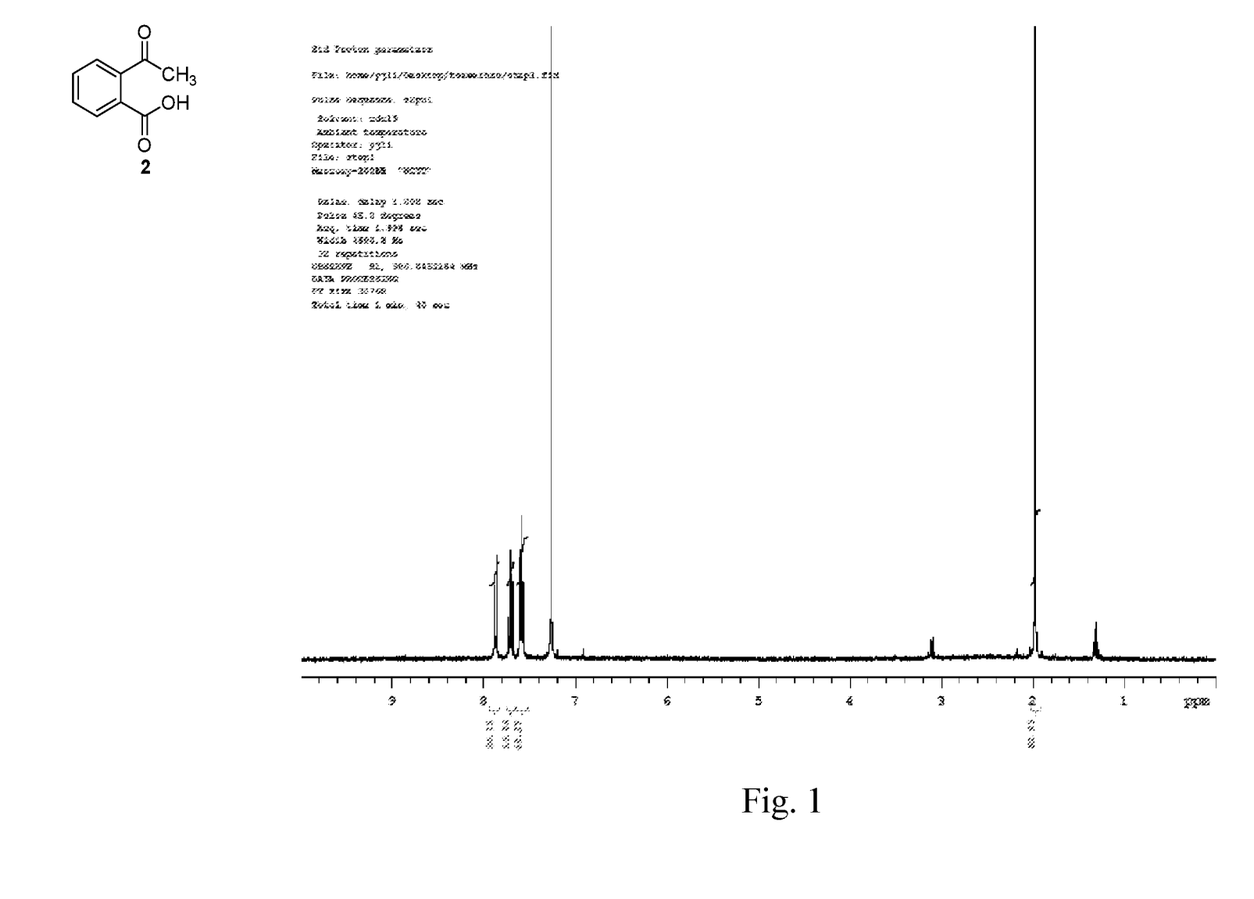
FIG. 1 is the nuclear magnetic resonance (NMR) diagram of 2-acetylbenzoic acid.

The crude product was added into ethyl acetate (107 mL), and the resultant mixture was heated to 55° C. to become a homogeneous solution. The homogeneous solution was slowly cooled to room temperature, and n-hexane (107 mL) was added thereinto to precipitate 2-acetylbenzoic acid. 43.6 g of 2-acetylbenzoic acid was obtained after filtration (yield: 39%). The NMR diagram of 2-acetylbenzoic acid is shown in FIG. 1.

Step (I-2): Preparation of 2-(2-Bromoacetyl)Benzoic Acid 2-acetylbenzoic acid (compound 2) (23.8 g, 0.145 moles) obtained in step (I-1) and acetic acid (CAS No.: 64-19-7; 15 mL) were added into a reactor (a 500 mL two-neck bottle), and the resultant mixture was stirred under room temperature for 10 minutes. Pyridinium tribromide (CAS No.: 39416-48-3; 1.3 eq, 67 g) was then added into the reactor. The reactor was heated to 40° C. to obtain a red homogeneous solution. The reaction was performed under 40° C. for 7 hours (the completion of reaction was determined by an NMR instrument). The reaction equation is as follows:

In the above reaction equation, the compound 3 represents 2-(2-bromoacetyl)-benzoic acid.

Figure 2:
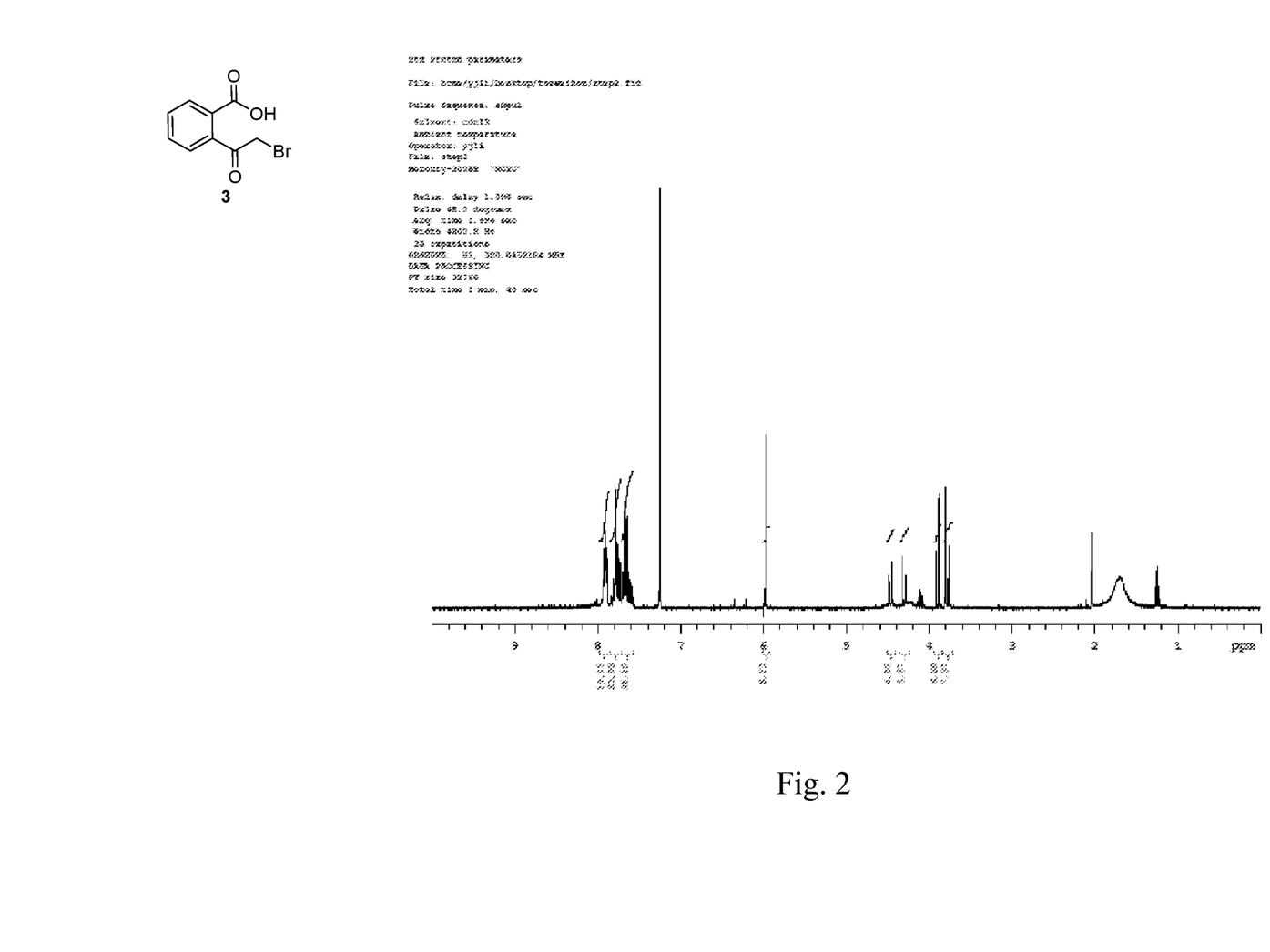
FIG. 2 is the nuclear magnetic resonance diagram of 2-(2-bromoacetyl)benzoic acid.

The reaction product was poured into 0° C. ice water after the completion of reaction, and the resultant mixture was stirred for 30 minutes. The mixture was then extracted with ethyl acetate and the organic phase was collected. The collected organic phase was washed with a 5% sodium thiosulfate (CAS No.: 7772-98-7) aqueous solution and saturated brine, dried over anhydrous sodium sulfate, and then concentrated in vacuum to obtain 32 g 2-(2-bromo-acetyl)benzoic acid (reddish brown crystalline solid). The NMR diagram of 2-(2-bromoacetyl)benzoic acid is shown in FIG. 2.

Step (I): Preparation of (Z)-3-(Bromomethylene) Isobenzofuran-1(3H)-One 2-(2-bromoacetyl)benzoic acid (compound 3) (38.1 g, 0.156 moles) dissolved in toluene (CAS No.: 108-88-3; 313 mL, 0.5 N) was added into a reactor (a 25 mL round-bottom bottle), and then trifluoroacetic anhydride (CAS No.: 407-25-0; 1.0 eq, 22.1 mL; abbreviation: TFAA) was added into the reactor. The resultant solution in the reactor was heated to 120° C. and refluxed for 8 hours by using the Dean-Stark reflux apparatus (the completion of reaction was determined by an NMR instrument). The reaction equation is as follows:

In the above reaction equation, the compound 4 represents (Z)-3-(bromomethylene)isobenzofuran-1(3H)-one.

Figure 3:
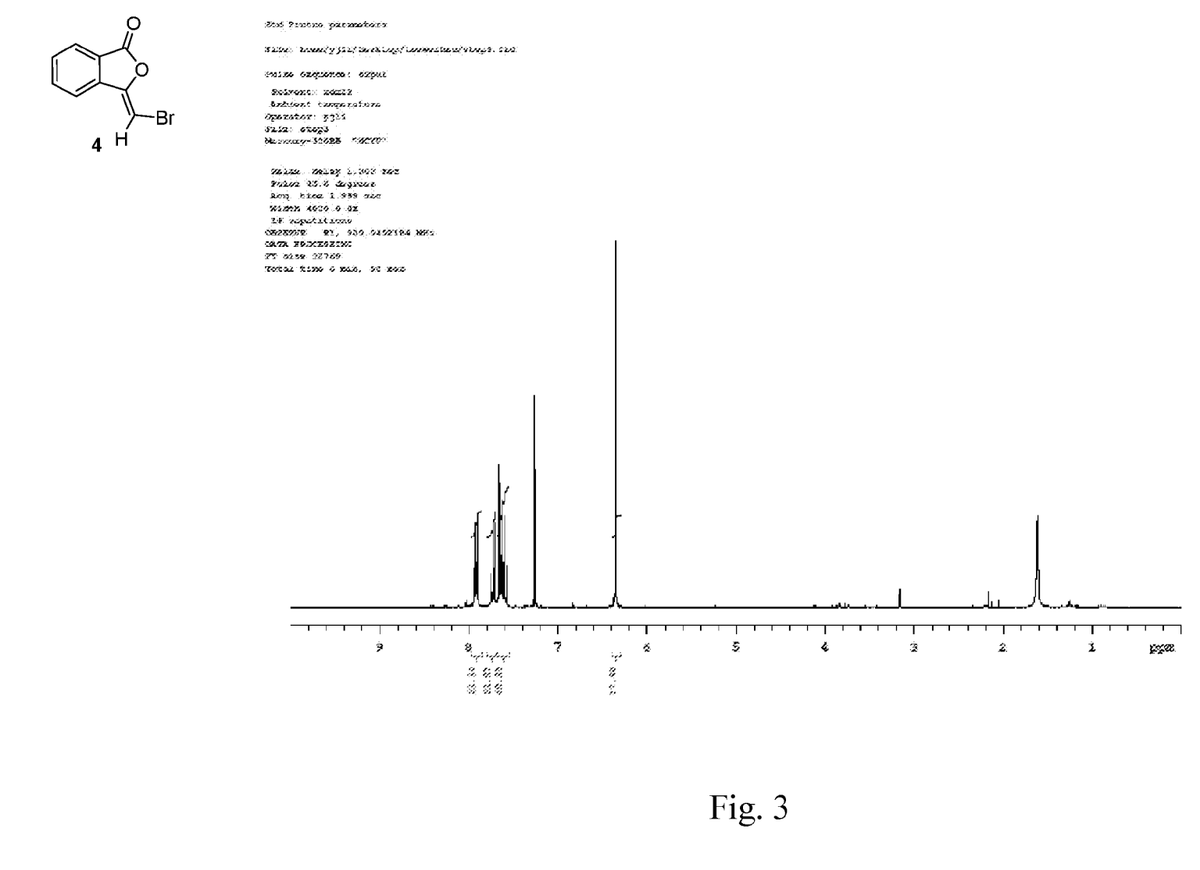
FIG. 3 is the nuclear magnetic resonance diagram of (Z)-3-(bromomethylene)-isobenzofuran-1(3H)-one.

The reaction product was concentrated to remove most of the toluene after the completion of the reaction. Ethyl acetate (100 mL×4) and the same amount of water were added into the concentrated reaction product for extraction. The aqueous layer was washed with a large quantity of water during the extraction until the aqueous layer was neutralized. Afterwards, the organic layer was collected and dried over anhydrous sodium sulfate, and then concentrated in vacuum to obtain a crude product. The crude product was purified by gradient elution (stationary phase:silica gel; eluant:n-hexane:ethyl ether=10:1) and determined by thin-layer chromatography (Rf value: 0.3; stationary phase: silica gel; mobile phase: n-hexane: ethyl ether=10:1) to obtain (Z)-3-(bromomethylene)isobenzofuran-1(3H)-one (compound 4; 17.6 g). The NMR diagram of (Z)-3-(bromomethylene) isobenzofuran-1(3H)-one is shown in FIG. 3.

Step (II): Preparation of (Z)-3-Butylideneisobenzofuran-1(3H)-One (Z)-3-(bromomethylene)isobenzofuran-1(3H)-one (compound 4) (1.0 g, 4.44 mmoles) dissolved in THF (CAS No.: 109-99-9; 5.6 mL) was added into a reactor (a flask roasted under nitrogen atmosphere). Then, $C_{27}H_{26}Cl_2NiP_2$ (CAS No.: 15629-92-2; 5 mol %; 130 mg) was added into the reactor. The resultant mixture was reacted at 0° C. for 20 minutes. Afterwards, a 2 N $C_3H_7MgCl$ solution (CAS No.: 2234-82-4; 1.54 eq, 1.3 mL) was added dropwise into the reactor at 0° C., and the resultant mixture was reacted for 10 minutes. The reaction equation is as follows:

In the above reaction equation, the compound 5 represents (Z)-3-butylideneisobenzofuran-1(3H)-one.

Figure 4:
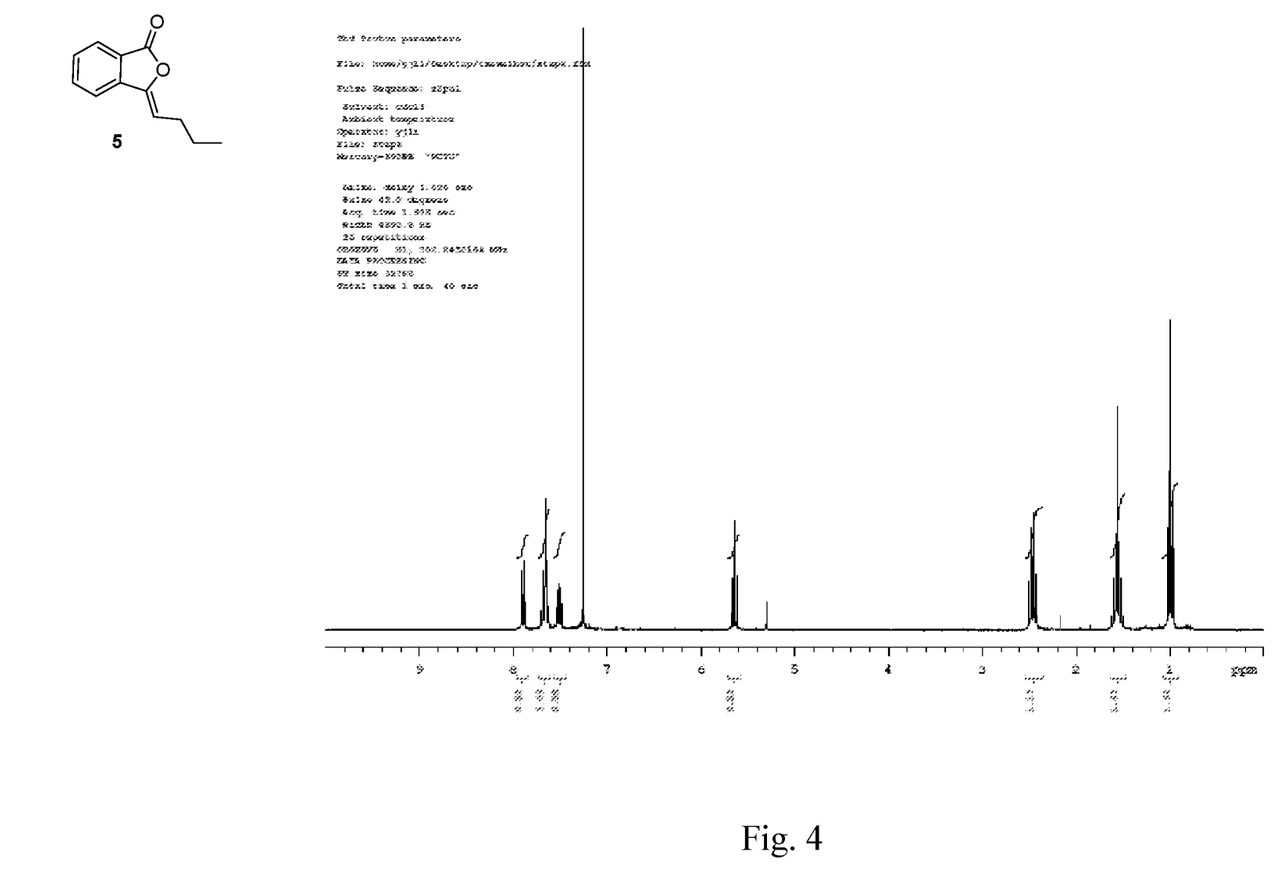
FIG. 4 is the nuclear magnetic resonance diagram of (Z)-3-butylideneisobenzofuran-1(3H)-one.

The reaction was monitored by thin-layer chromatography (stationary phase:silica gel; mobile phase:n-hexane: ethyl ether=5:1; Rf value: 0.5). After the reaction was completed, it was quenched by adding ice water into the reactor. About 20 minutes later, 2M hydrochloric acid solution was used to adjust the pH value of the reaction product to about 6. The resultant reaction product was extracted with ethyl acetate (20 mL×3). The organic layer was washed with the same amount of saturated brine. Afterwards, the organic layer was collected and dried over anhydrous sodium sulfate, and then concentrated in vacuum to obtain a crude product. The crude product was purified by gradient elution (stationary phase:silica gel; eluant:n-hexane:ethyl ether=5:1) to obtain (Z)-3-butylideneisobenzofuran-1(3H)-one (543 mg; yield: 65%). The NMR diagram of (Z)-3-butylideneisobenzofuran-1(3H)-one is shown in FIG. 4.

The above example is used to illustrate the principle and efficacy of the present invention and show the inventive features thereof. People skilled in this field may proceed with a variety of modifications and replacements based on the disclosures and suggestions of the invention as described without departing from the principle and spirit thereof. Therefore, the scope of protection of the present invention is that as defined in the claims as appended.

What is claimed is:
1. A method for preparing the following compound 5:

the method comprises the following steps:
(I-1) reacting the following compound 1 with malonic acid in the presence of a tertiary amine at a temperature ranging from 50° C. to 90° C. to obtain the following compound 2;

1

2

(1-2) reacting the compound 2 with a brominating agent in a carboxylic acid at a temperature ranging from 30° C. to 50° C. to obtain the following compound 3;

3

(I) reacting a halogenated carboxylic acid anhydride with the compound 3 at a temperature ranging from 50° C. to 140° C. to obtain the following compound 4; and

4

(II) reacting the compound 4 with a compound of (R2)MgX at a temperature ranging from −10° C. to 10° C. to obtain the compound 5,
wherein, R2 is propyl; and
X is Cl⁻, Br⁻ or I⁻.

2. The method as claimed in claim 1, wherein in step (I) the temperature ranges from 100° C. to 130° C.

3. The method as claimed in claim 1, wherein in step (II) the temperature ranges from −5° C. to 5° C.

4. The method as claimed in claim 1, wherein the halogenated carboxylic acid anhydride is selected from the group consisting of monofluoroacetic anhydride, difluoroacetic anhydride, trifluoroacetic anhydride, pentafluoropropionic anhydride, heptafluorobutyric anhydride, perfluoropentanoic anhydride, perfluorohexanoic anhydride, chlorodifluoroacetic anhydride, monochloroacetic anhydride, dichloroacetic anhydride, trichloroacetic anhydride, pentachloropropionic anhydride, heptachlorobutyric anhydride, perchloropentanoic anhydride, perchlorohexanoic anhydride, and combinations thereof.

5. The method as claimed in claim 4, wherein the halogenated carboxylic acid anhydride is trifluoroacetic anhydride.

6. The method as claimed in claim 1, wherein the reaction of step (I) is carried out in toluene, and the reaction of step (II) is carried out in an inert solvent selected from the group consisting of diethyl ether, tetrahydrofuran (THF), 2-methyl tetrahydrofuran, and combinations thereof.

7. The method as claimed in claim 1, which further comprises the following purification steps prior to step (II): extracting the reaction product of step (I) with ethyl acetate, collecting the organic phase, and filtering the organic phase and concentrating the obtained filtrate to obtain the compound 4.

8. The method as claimed in claim 1, which further comprises the following purification steps after step (II):
mixing the reaction product of step (II) with ice water to provide a first mixture having a pH value of 5 to 7;
extracting the first mixture with ethyl acetate and collecting the organic phase; and
filtering the organic phase and concentrating the obtained filtrate to obtain the compound 5.

9. The method as claimed in claim 1, wherein the tertiary amine is a trialkyl amine or a trialkoxyamine.

10. The method as claimed in claim 9, wherein the tertiary amine is triethylamine.

11. The method as claimed in claim 1, wherein the brominating agent is selected from the group consisting of bromine, pyridinium tribromide, N-bromosuccinimide and combinations thereof.

12. The method as claimed in claim 11, wherein the brominating agent is pyridinium tribromide.

13. The method as claimed in claim 1, wherein the carboxylic acid is selected from the group consisting of formic acid, acetic acid, propionic acid, butyric acid and combinations thereof.

14. The method as claimed in claim 13, wherein the carboxylic acid is acetic acid.

15. The method as claimed in claim 1, which further comprises the following purification steps prior to step (I-2):
extracting the reaction product of step (I-1) with ethyl acetate and collecting the organic phase;
filtering the organic phase and concentrating the obtained filtrate;
mixing the concentrated filtrate with ethyl acetate and heating the obtained mixture to a temperature between 50° C. and 60° C. to provide a second mixture; and
cooling the second mixture down to room temperature and mixing the same with n-hexane to precipitate the compound 2.

16. The method as claimed in claim 15, which further comprises adjusting the pH value of the reaction product of step (I-1) to 5 to 7 prior to the extraction with ethyl acetate.

17. The method as claimed in claim 1, which further comprises the following purification steps after step (I-2):
extracting the reaction product of step (I-2) with ethyl acetate and collecting the organic phase; and
filtering the organic phase and concentrating the obtained filtrate to obtain the compound 3.

* * * * *